(12) United States Patent
Lehtinen et al.

(10) Patent No.: US 9,927,384 B2
(45) Date of Patent: Mar. 27, 2018

(54) METHOD AND AN ARRANGEMENT IN CONDITION MONITORING OF AN ELEVATOR ROPE

(71) Applicants: Hannu Lehtinen, Numminen (FI); Mikko Puranen, Riihimaki (FI)

(72) Inventors: Hannu Lehtinen, Numminen (FI); Mikko Puranen, Riihimaki (FI)

(73) Assignee: KONE CORPORATION, Helsinki (FI)

( * ) Notice: Subject to any disclaimer, the term of this patent is extended or adjusted under 35 U.S.C. 154(b) by 330 days.

(21) Appl. No.: 14/729,751

(22) Filed: Jun. 3, 2015

(65) Prior Publication Data
US 2015/0362450 A1 Dec. 17, 2015

(30) Foreign Application Priority Data
Jun. 17, 2014 (FI) ..................................... 20145568

(51) Int. Cl.
*B66B 7/12* (2006.01)
*G01N 27/20* (2006.01)
(Continued)

(52) U.S. Cl.
CPC .............. *G01N 27/20* (2013.01); *B66B 5/00* (2013.01); *B66B 7/1223* (2013.01); *B66B 19/02* (2013.01)

(58) Field of Classification Search
CPC ......... B66B 7/1223; B66B 5/00; B66B 19/02; G01N 27/20
(Continued)

(56) References Cited

U.S. PATENT DOCUMENTS

| 3,693,784 A | 9/1972 | Holmes |
| 2002/0194935 A1 * | 12/2002 | Clarke .................. B66B 7/1223 73/862.391 |

(Continued)

FOREIGN PATENT DOCUMENTS

| CA | 2910989 A1 * | 12/2014 | ............. B66B 19/02 |
| EP | 2789563 A1 * | 10/2014 | ............. B66B 13/22 |

(Continued)

OTHER PUBLICATIONS

Extended European Search Report dated Nov. 9, 2015 issued in corresponding European Application No. 15169345.4.
Finnish Search Report for FI 20145568 dated Feb. 12, 2015.

*Primary Examiner* — David Warren
(74) *Attorney, Agent, or Firm* — Harness, Dickey & Pierce, PLC

(57) ABSTRACT

The invention relates to a method in rope condition monitoring of an elevator, in which method at least the following steps are performed: elevator suspension and/or transmission ropes are reeled and packed on a rope storage unit, and thereafter electrical resistance between a first point and a second point of elevator suspension and/or transmission ropes is measured first time, and thereafter a threshold value is determined based on the measurement, and thereafter rope is delivered into an installation site, and thereafter electrical resistance between the first point and the second point of said suspension and/or transmission ropes is measured second time, and thereafter results of said second time measurement are compared with said threshold value, and if said second time measurement meets said threshold value, predetermined actions are carried out. The invention also relates to an arrangement in rope condition monitoring of an elevator.

24 Claims, 2 Drawing Sheets

(51) Int. Cl.
  *B66B 5/00* (2006.01)
  *B66B 19/02* (2006.01)
(58) Field of Classification Search
  USPC .......................................... 73/810; 187/391
  See application file for complete search history.

(56) References Cited

U.S. PATENT DOCUMENTS

| | | | |
|---|---|---|---|
| 2003/0121729 A1* | 7/2003 | Heinz | B66B 7/062 |
| | | | 187/254 |
| 2005/0063449 A1* | 3/2005 | Lustenberger | B66B 7/1223 |
| | | | 374/4 |
| 2007/0180925 A1* | 8/2007 | Stucky | B66B 7/062 |
| | | | 73/810 |
| 2008/0223668 A1* | 9/2008 | Stucky | B66B 7/1223 |
| | | | 187/393 |
| 2010/0133046 A1* | 6/2010 | Allwardt | B66B 7/08 |
| | | | 187/251 |
| 2011/0000746 A1 | 1/2011 | Pelto-Huikko et al. | |
| 2011/0148442 A1* | 6/2011 | Berner | B66B 7/1223 |
| | | | 324/691 |
| 2011/0266097 A1 | 11/2011 | Valjus et al. | |
| 2012/0090924 A1* | 4/2012 | Odermatt | B66B 7/062 |
| | | | 187/251 |
| 2013/0062146 A1* | 3/2013 | Nolting | B66B 7/062 |
| | | | 187/251 |
| 2013/0153340 A1* | 6/2013 | Dold | B66B 7/1223 |
| | | | 187/393 |
| 2013/0207668 A1* | 8/2013 | Fargo | G01N 27/20 |
| | | | 324/601 |
| 2014/0182975 A1* | 7/2014 | Ikonen | B66B 5/0031 |
| | | | 187/251 |
| 2015/0063415 A1 | 3/2015 | Garfinkel et al. | |
| 2015/0191332 A1* | 7/2015 | Kere | B66B 7/062 |
| | | | 187/251 |
| 2015/0298941 A1* | 10/2015 | Dold | B66B 7/062 |
| | | | 187/393 |
| 2015/0362450 A1* | 12/2015 | Lehtinen | B66B 19/02 |
| | | | 187/391 |
| 2015/0375963 A1* | 12/2015 | Sun | B66B 7/1223 |
| | | | 187/254 |
| 2016/0002006 A1* | 1/2016 | Sun | B66B 7/1223 |
| | | | 187/254 |
| 2016/0023865 A1* | 1/2016 | Fargo | B66B 7/1223 |
| | | | 324/693 |
| 2016/0152445 A1* | 6/2016 | Lehtinen | B66B 7/062 |
| | | | 187/393 |
| 2016/0221796 A1* | 8/2016 | Puranen | B66B 7/085 |
| 2016/0229667 A1* | 8/2016 | Cereghetti | B66B 7/1223 |
| 2017/0029249 A1* | 2/2017 | Robibero | B66B 7/1215 |

FOREIGN PATENT DOCUMENTS

| | | | | |
|---|---|---|---|---|
| WO | WO-2009090299 A1 | | 7/2009 | |
| WO | WO 2012030332 A1 | * | 3/2012 | .......... B66B 7/1223 |
| WO | WO 2013119203 A1 | * | 8/2013 | ............ D07B 1/145 |
| WO | WO 201 31 51 52 | * | 10/2013 | .......... B66B 7/1223 |
| WO | WO-2013151525 A1 | | 10/2013 | |
| WO | WO-2014/064021 A1 | | 5/2014 | |
| WO | WO 2015126358 A1 | * | 8/2015 | .......... B66B 7/1223 |

* cited by examiner

METHOD AND AN ARRANGEMENT IN CONDITION MONITORING OF AN ELEVATOR ROPE

This application claims priority to Finnish Patent Application No. 20145568 filed on Jun. 17, 2014, the entire contents of which are incorporated herein by reference.

FIELD OF THE INVENTION

The invention relates to damage detection and condition monitoring of an elevator rope. The rope is, in particular, a rope for an elevator meant for transporting passengers and/or goods.

BACKGROUND OF THE INVENTION

Storing of an elevator rope may be needed in various stages of its lifetime. The storing is conventionally implemented by forming a rope reel of the rope so that it can be stored and/or transported as a compact unit. In the field of elevators, storing is usually needed for transporting the rope from production to the site, and further to the specific installation location where the rope can be unwound and installed in the elevator.

There are a lot of potential places in logistics chain as well as during installation where rope can be damaged without having visual indication about failure. Such invisible damages include mechanical damages during transportation, environmental effects that can cause extra stress or overload of the rope, specified temperature- and/or humidity levels exceeded during logistics chain, such as storing the rope under the sun, as well as mechanical damages during installation such as tight bending of punch or rope leaves in high compression.

Ropes comprising load bearing members made of twisted wires or equivalents are typically irreversibly flexible such that after bending the rope into a curve, it does not reverse back to its original form and the rope is easy to wind around a drum where it can be stored until a later unwinding. Such wires are typically uncoated and easy to inspect visually. However, there are also ropes which are rod-like and have a straight form when they are in rest state. Such a rope is presented in patent publication WO 2009090299 A1, for instance. This kind of rope is relatively rigid, but elastically bendable, and the rope self-reverses back to a straight form from bent form in rest state after all bending directed to it ceases. In this kind of rope load bearing components are inside the coating surface. Therefore, visual check of potential damages might be sometimes difficult or even impossible. There is a need for a method with which load bearing components inside the coating can be inspected and condition of the rope reliably monitored without visual inspection.

BRIEF DESCRIPTION OF THE INVENTION

The object of the invention is to introduce an improved method and an arrangement in condition monitoring of an elevator rope. The object of the invention is, inter alia, to solve drawbacks of known solutions and problems discussed later in the description of the invention. It is also an object to allow a cost-effective and reliable condition monitoring method and an arrangement for an elevator suspension and/or transmission rope comprising composite materials allowing the in situ monitoring of damage before the elevator suspension and/or transmission rope is installed in an elevator.

Embodiments are presented which, inter alia, facilitate simple, safe and efficient damage detection of non-metallic, preferably carbon-fibre-reinforced polymer composite load bearing parts in said elevator ropes. Also, embodiments are presented, where invisible damages including mechanical damages during transportation, environmental effects that has caused extra stress or overload of the rope, specified temperature- and/or humidity levels exceeded during logistics chain, such as storing the rope under the sun, as well as mechanical damages during installation such as tight bending of punch or rope left in high compression are detected. Also, embodiments are presented, where reliable in situ condition monitoring of the ropes throughout the elevator life, even before the rope is installed into an elevator, is possible and safety of the elevator is improved.

It is brought forward a new method and an arrangement in condition monitoring of an elevator rope. In a preferred embodiment of the method at least the following steps are performed: elevator suspension and/or transmission ropes are reeled and packed on a rope storage unit, and thereafter, electrical resistance between a first point and a second point of elevator suspension and/or transmission ropes is measured first time, and thereafter, a threshold value is determined based on the measurement, and thereafter, the rope is delivered into an installation site, and thereafter, electrical resistance between the first point and the second point of said suspension and/or transmission ropes is measured second time, and thereafter results of said second time measurement are compared with said threshold value, and if said second time measurement meets said threshold value, predetermined actions are carried out.

In a preferred embodiment, electrical resistance between the first point and the second point of said suspension and/or transmission ropes is measured first time in the production site of the rope.

In a preferred embodiment, electrical resistance between the first point and the second point of said suspension and/or transmission ropes is measured first time and second time before unwinding the ropes from the rope storage unit.

In a preferred embodiment, electrical resistance measurement result is marked on delivery note or on the rope storage unit or on the rope itself or in a memory/database of a computer application.

In a preferred embodiment, electrical resistance between the first point and the second point of said suspension and/or transmission ropes is measured first time and/or second time while the ropes are stored on the rope storage unit comprising a rope reel formed by a rope wound in a spiral form and a support body provided with an inner space inside which the rope reel is positioned supported by the support body.

In a preferred embodiment, electrical resistance between the first point and the second point of said suspension and/or transmission ropes is measured second time before unwinding the ropes from the rope storage unit.

In a preferred embodiment, electrical resistance between the first point and the second point of said suspension and/or transmission ropes is measured second time before installation of the ropes into the elevator.

In a preferred embodiment, electrical resistance between the first point and the second point of said suspension and/or transmission ropes is measured when rope installation is ready, before mounting the ropes into rope terminals.

In a preferred embodiment, the first point and second point are points of a non-metallic load bearing part of the suspension and/or transmission rope, or points of several electrically connected non-metallic load bearing parts of the suspension and/or transmission ropes.

In a preferred embodiment, the first point and second point are points of load bearing parts of the suspension and/or transmission ropes made of fiber-reinforced polymer matrix composite material, such as carbon fiber-reinforced polymer matrix composite, preferably unidirectional carbon fiber-reinforced polymer matrix composite.

In a preferred embodiment, if the second time measurement value meets said threshold value between a first point and a second point of elevator suspension and/or transmission ropes, an error signal is given.

In a preferred embodiment, the rope identification code and error level indication are shown for each rope on the LED or LCD display of a rope condition monitoring device if said error signal is given.

In a preferred embodiment, if the error signal is given the rope is judged to be damaged during transportation or storing and the rope is prevented to be installed into elevator.

In a preferred embodiment, if the second time measurement does not meet said threshold value, the rope is installed in the elevator.

It is also brought forward a new arrangement in condition monitoring of an elevator rope. In a preferred embodiment of the arrangement in condition monitoring of an elevator rope, the arrangement comprises one or more suspension and/or transmission ropes, each rope comprising one or more load bearing parts, a rope storage unit comprising a rope reel, rope condition monitoring means, in which arrangement the rope condition monitoring means are arranged to perform the following steps: elevator suspension and/or transmission ropes are reeled and packed in a rope storage unit, and thereafter electrical resistance between a first point and a second point of elevator suspension and/or transmission ropes is measured first time, and thereafter a threshold value is determined based on the measurement, and thereafter the rope is delivered into an installation site, and thereafter electrical resistance between the first point and the second point of the suspension and/or transmission ropes is measured second time, and thereafter results of the second time measurement are compared with the threshold value, and if the second time measurement meets the threshold value, predetermined actions are carried out.

In a preferred embodiment, the rope condition monitoring means is used to measure electrical resistance between the first point and the second point of said suspension and/or transmission ropes is measured first time in the production site of the rope.

In a preferred embodiment, the rope condition monitoring means is used to measure electrical resistance between the first point and the second point of the suspension and/or transmission ropes first time before unwinding the ropes from the rope storage unit.

In a preferred embodiment, the rope condition monitoring means is used to measure electrical resistance between the first point and the second point of the suspension and/or transmission ropes first time and/or second time while the ropes are stored on the rope storage unit.

In a preferred embodiment, the rope condition monitoring means is used to measure electrical resistance between the first point and the second point of the suspension and/or transmission ropes after unwinding the ropes from the rope storage unit and installation of the ropes into an elevator.

In a preferred embodiment, a rope storage unit comprises a rope reel, formed by a rope wound in a spiral form, and a support body provided with an inner space inside which the rope reel is positioned supported by the support body.

In a preferred embodiment, the first point and the second point are points of a non-metallic load bearing part of the suspension and/or transmission rope, or points of several electrically connected non-metallic load bearing parts of the suspension and/or transmission ropes.

In a preferred embodiment, the first point and the second point are points of load bearing parts of said suspension and/or transmission ropes made of fiber-reinforced polymer matrix composite material, such as carbon fiber-reinforced polymer matrix composite, preferably unidirectional carbon fiber-reinforced polymer matrix composite.

In a preferred embodiment, if the second time measurement value meets the threshold value between a first point and a second point of elevator suspension and/or transmission ropes, an error signal is given by said rope condition monitoring means.

In a preferred embodiment, the rope condition monitoring means comprises a rope condition monitoring device and the rope identification code and error level indication are shown for each rope on the LED or LCD display of the rope condition monitoring device if said error signal is given.

In a preferred embodiment, the rope condition monitoring means comprises a data logger-type condition monitoring device. The device is connected to the rope storage unit, for instance to the rope reel after rope manufacturing.

In a preferred embodiment, if an error signal is given the rope is judged to be damaged during transportation or storing and the rope is prevented to be installed into elevator.

In a preferred embodiment, if the second time measurement does not meet a threshold value, the rope is installed in the elevator.

In a preferred embodiment, the rope is reeled and packed in production on an installation package.

In a preferred embodiment, rope end blocks are installed into rope ends. Rope end blocks are connected into load bearing components of the rope. Rope end blocks can be the same elements that are used in condition monitoring when the elevator is used for transporting passengers and/or goods.

Rope condition monitoring means monitors the status of each rope, said threshold value and said measurement values at predefined time intervals, preferably once per second.

In a preferred embodiment, carbon-fiber-reinforced polymer composite load bearing parts are bent and the electrical resistance of the parts is measured. A correlation between the increase in the electrical resistance and the decrease in the bending modulus can be observed. For unidirectional carbon-fiber-reinforced polymer composites, the longitudinal electrical resistance of unidirectional fiber is much lower than the transverse resistance, and the damage in the composite material can be detected by measuring the one or the other. Electrical resistance is a good damage sensor for carbon/epoxy laminates, for instance, especially for the detection of fiber breakage.

In a preferred embodiment there are three distinctive phases in the electrical resistance change. First, the electrical resistance increases slightly when the stress increases. This is normal aging process. When the stress further increases, individual fibers in carbon-fibre-reinforced polymer begin to crack and the electrical resistance will increase a lot faster, causing the change in the slope of the stress-electrical resistance curve. When the fibers fail completely, the electrical resistance increases rapidly.

In a preferred embodiment a DC measurement method measuring electrical resistance, is used. The DC measurement method is mainly sensitive to fiber failures, while AC measurements measuring electrical capacitance provide information on the development of inter-layer matrix cracks and inter-layer delamination. Therefore, with unidirectional fiber composites, such as within load bearing parts of light-weight elevator ropes, electrical resistance measurement method provides more useful information in light of the safe use of the elevator suspension and/or transmission ropes.

In a preferred embodiment, unidirectional carbon-fibre-reinforced polymer is used as a load carrying element instead of steel in a light-weight elevator suspension and/or transmission rope. According to the invention, condition monitoring method and an arrangement for ropes with load-bearing parts made of carbon-fibre-reinforced polymer composite has been developed. Electrical resistance is a good indicator for the overall condition of carbon-fibre-reinforced polymer composite. Resistance changes if strain of the fibre is increased or if fibre breaks occur. Resistance change in an elevator rope can be used to detect rope wear or damage.

In a preferred embodiment the rope condition monitoring arrangement is used in elevators with counterweight, however as well being applicable in elevators without counterweight. In addition, it can also be used in conjunction with other hoisting machines, e.g. as a crane suspension and/or transmission rope. The low weight of the rope provides an advantage especially in acceleration situations, because the energy required by changes in the speed of the rope depends on its mass. The low weight further provides an advantage in rope systems requiring separate compensating ropes, because the need for compensating ropes is reduced or eliminated altogether. The low weight also allows easier handling of the ropes.

In a preferred embodiment condition monitoring means comprises condition monitoring device comprising independent adjustable constant current supplies for each rope. In a learning phase, measurement current is adjusted to achieve desired voltage over the rope, advantageously 2.5 V, for instance. Learning sequence is activated only once, immediately after commissioning of the elevator. When the measurement current is adjusted and set, the voltage over the rope is measured through the lifetime of the rope so possible voltage changes, i.e., resistance changes are detected. Initial values of current and voltage are saved in a non-volatile memory. In a preferred embodiment one condition monitoring device is able to monitor multiple, up to twelve, or even more, ropes.

In a preferred embodiment condition monitoring device can identify several, preferably at least three different faults. Normal rope wear causes minor, preferably 2-5% change in resistance. Broken rope coating causes preferably low resistance, and breaks in carbon-fibre-reinforced polymer or loose measurement wire causes preferably high resistance.

In a preferred embodiment, said rope condition monitoring device is used to measure resistance changes of the rope before installation of the rope to the elevator. Preferably resistance of the rope increases when the strain of the rope increases. Resistance change is reversible if fibre breaks do not occur, irreversible resistance change preferably indicates rope damage and fibre breaks. Bad measuring wire contact increases resistance fluctuation. This may cause some false alarms, but from safety point of view, this is on the safe side.

The filtered results are compared to the threshold values and if said filtered results meet said threshold values, an error code as follows.

Level 1: Minor error, if deviation from said threshold values less than 5%.

Level 2: Low resistance, if deviation from said threshold values is equal to or less than 20%: Rope coating is worn or broken and rope grounded.

Level 3: High resistance, if deviation from the threshold values is over 20%: Rope load-bearing part is broken or measurement wires disconnected.

In a preferred embodiment error signals are shown on a display so that the elevator rope installation can be altered or the elevator rope can be taken out of service, depending on the severity of the fault. Hence the safety of the elevator is improved.

In a preferred embodiment the elevator lightweight rope comprises one or more, preferably at least four unidirectional carbon fiber-reinforced-polymer load-bearing parts covered with polyurethane coating. In case of four load-bearing parts, the rope can be electrically modeled as four resistors. Preferred solution is to measure one rope as a single resistance. In that way measuring arrangements are kept simple and the method is also more reliable, because the number of wires and connections is minimized. This method requires simple and reliable solutions to a) short-circuit carbon fiber-reinforced-polymer load-bearing parts and b) connect the measuring wires to the rope, preferably by self-tapping screws screwed between the load-bearing parts in such way, that the screw acts as an electrically conductive path between adjacent load-bearing parts. At the second end of the rope, preferably the counterweight end, three screws are preferably used to short-circuit all of the strands. At the first end of the rope, preferably the car end, two outermost strands are preferably connected together, and measuring wires are inserted under these two screws with a split ring connector. With this arrangement, all carbon fiber-reinforced-polymer load-bearing parts are monitored and the whole rope is seen as a single resistor.

In a preferred embodiment the monitoring device is based on a microcontroller. The resistance can not be measured directly but a constant current source and voltage measurement are used instead.

In a preferred embodiment the device has numeric display and several, preferably at least four LEDs that are used as a status display and an output and memory card socket for data logging.

In a preferred embodiment one device can monitor several ropes, preferably up to twelve ropes, or even more. In a preferred embodiment current source is controlled by a digital to analog-converter DAC. Preferably the DAC driven by the microcontroller provides a reference voltage to the operational amplifier, which in turn adjusts the gate voltage of the MOS-transistor. Preferably gate voltage determines the current that flows through the MOS-transistor. Preferably feedback from the shunt resistor to the operational amplifier ensures that the voltage at the reference point is the same as the control voltage from the DAC. RC-filters are used to prevent oscillations.

In a preferred embodiment the DAC used has several, preferably at least twelve, or even more output sources. To avoid drifting and interference caused by fluctuating operating voltage, reference voltage for shunt resistor and DAC must come preferably from the same point. This totally eliminates the changes in the measurement current fed to the ropes caused by possibly poorly regulated operating voltage.

In a preferred embodiment, described measurements and evaluation of the rope condition can also be done automatically using data logger-type condition monitoring device. The device is connected to the rope storage unit, for instance to the rope reel after rope manufacturing, and it is left in place until rope is installed. The device operates independently, and monitors resistance changes. If pre-set threshold for allowed resistance change is exceeded, warning is shown on user interface, for example LED light or LCD display.

The elevator as describe anywhere above is preferably, but not necessarily, installed inside a building. The car is preferably traveling vertically. The car is preferably arranged to serve two or more landings. The car preferably responds to calls from landing and/or destination commands from inside the car so as to serve persons on the landing(s) and/or inside the elevator car.

Preferably, the car has an interior space suitable for receiving a passenger or passengers, and the car can be provided with a door for forming a closed interior space.

BRIEF DESCRIPTION OF THE DRAWINGS

In the following the present invention will be described in more detail by way of example and with reference to the attached drawings, in which.

DETAILED DESCRIPTION

Figure 1:
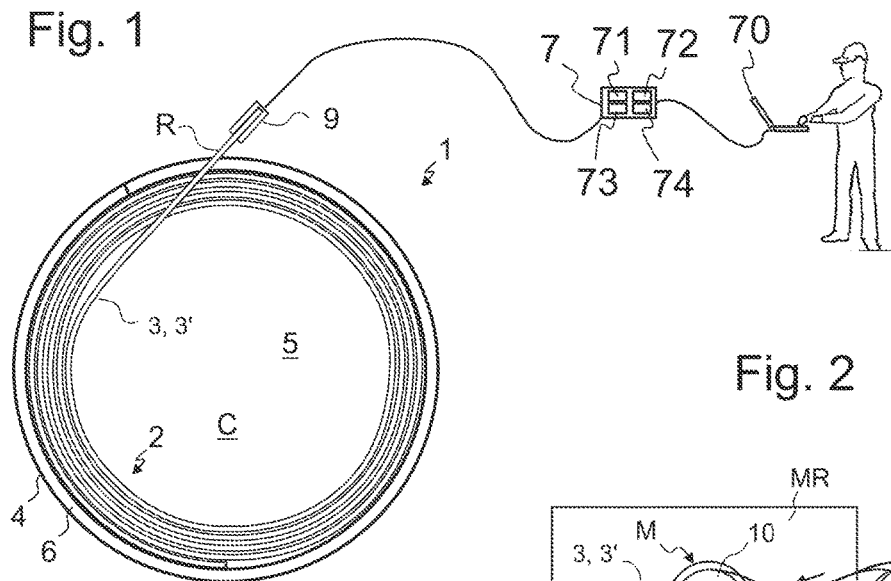
FIG. 1 illustrates overview of the arrangement in condition monitoring of an elevator rope where method steps of the invention can be performed.

FIG. 1 illustrates overview of the arrangement in condition monitoring of an elevator rope where method steps of the invention can be performed. The rope storage unit 1 comprises a rope reel 2, formed by a rope 3, 3' wound in a spiral form. The rope 3, 3' has two ends, i.e. a first end and a second end. A rope end block 9 is attached on said end face side of the elevator rope first end. Electrical rope condition monitoring means 7 are connected to the rope 3, 3' via said rope end block 9.

Preferably rope end block 9 is a single piece structure manufactured from plastics or some other electrically non-conductive material, such as from thermoplastics polymer or thermosetting polymer. Preferably rope end block 9 comprises a first frame portion attached to the elevator rope end with fastening means. It is thus possible for the fastening means to pass through the openings in the first frame portion of the rope end block 9. The fastening means can advantageously be made of metal or of some other suitable electrically conductive material. The fastening means are advantageously screws or bolts with nuts. The fastening to the rope can be done by drilling bores in the rope 3, 3' and fastening with screws or bolts.

In a preferred embodiment said rope end block 9 comprises one or more short circuit elements attached to said rope end block 9 with fastening means. It is thus possible for the fastening means to pass through the openings in the short circuit elements. The short circuit elements such as short circuit plates as well as the fastening means are advantageously made of metal or of some other suitable electrically conductive material. The fastening means for attaching short circuit elements are advantageously the same screws or bolts used to attach the rope end block 9 to the rope 3, 3'.

The rope is preferably a belt-like rope. That is, the rope 3, 3' has width larger than thickness thereof in transverse direction of the rope 3, 3'. Then, the rope 3, 3' is wound in said spiral form by bending it around an axis extending in width-direction of the rope 3, 3'. Thus, the rope 3, 3' settles easily in the spiral form. Due to the belt-like construction, it resists from strongly bending away from a coplanar configuration. Thus, the rope reel 2 maintains well its spiral reel configuration and is not prone to unwind accidentally. In this way, also formation of twist can be avoided.

Preferably the rope storage unit 1 comprises a support body 4 provided with an inner space 5 inside which the rope reel 2 is positioned supported by the support body 4. The rope 3, 3' is a rigid rope, more specifically it has a rod-like structure. The rod, i.e. the rope 3, 3' has a straight form when in rest state. In particular, the rod i.e. the rope 3, 3' is elastically bendable away from the straight form. Thereby, it self-reverses to straight form from bent form. For this reason, the rope 3, 3' is under substantial bending tension in said spiral form. The support body 4 comprises one or more support members 6. The support members 6 delimit and surround radially, in particularly its/their inner face(s), said inner space 5 said rope reel 4. In the embodiment as illustrated in FIG. 1 the support body 4 comprises a single support member 6 said inner space 5 and surrounding radially said rope reel 4. The outer rim of the rope reel 2 radially compresses against said one or more support members 6 as an effect of said bending tension, said support member 6 thereby delimiting the radius of the rope reel 2 from expanding forced by the bending tension. Thereby said support member 6 blocks the rope of the rope reel 2 from straightening.

The support body 4 preferably comprises a support drum formed by said one or more support members 6, which delimit(s) a cylindrical inner space 5. The support drum is made of one or more bent fiberboard members. In the embodiment of FIG. 1 the support drum is made of one fiberboard member 6 bent into curved shape, but the support drum can be made of several fiberboard members 6 bent into curved shape, fiberboard members 6 together forming said drum. The curved form is an arc form providing an inner radius of curvature for the support member 6, which corresponds to that of the outer radius of the rope reel 2 radially compressing against the support member 6. Said cylindrical inner space 5 has in axial direction an open or at least openable side so that the rope 3, 3' can be positioned inside it via the open side as a fully in spiral form wound rope reel 2.

Said rope 3, 3' is preferably such that it comprises one or more load bearing members 8, 8', 8", 8''' made of composite material comprising reinforcing fibers f in polymer matrix m. Preferably, the reinforcing fibers f are carbon fibers. Thus a lightweight rope with high tensile stiffness can be obtained. Said load bearing member(s) 8, 8', 8", 8''' is/are parallel with the length direction of the rope. For example with this structure the rope 3, 3' is elastically bendable away from the straight form. Thereby, it self-reverses to straight form from bent form However, it is rigid to bend and therefore using the rope storage unit 1 to store this rope is advantageus. Also, using other reinforcing fibers as fibers f of the composite material such as glass fiber, can provide these properties for the rope 3, 3'. Said reinforcing fibers are preferably also parallel with the length direction of the rope so the tensile stiffness can be maximized. It is preferable, that each of said load bearing member(s) 8, 8', 8", 8''' has width w larger than thickness t thereof as measured in width-direction of the rope 3, 3'. In this way a large cross-sectional area for the load bearing member/parts 3, 3' is achieved, without weakening the bending capacity around an axis extending in the width (extending from left to right in FIG. 3) direction of the rope 3, 3'. A small number of wide load bearing members comprised in the rope leads to efficient utilization of the width of the rope, thus making it possible to keep the rope width of the rope in advantageous limits.

Figure 2:
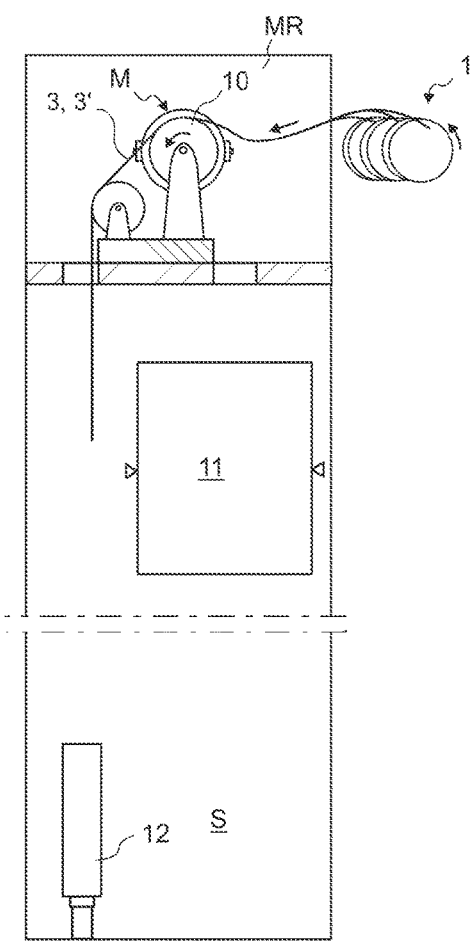
FIG. 2 illustrates an overview of the arrangement in installation of ropes into an elevator.

FIG. 2 illustrates an overview of the arrangement in installation of ropes into an elevator. Before the ropes are installed into an elevator, in situ condition monitoring of the ropes are performed. If the second time measurement on installation site does not meet said threshold value, the rope is installed into the elevator. The rope storage units 1 are provided. A rope 3, 3' is unwound from each rope storage unit 1 as illustrated in FIG. 2, and thereafter connected to movable elevator units 11, 12, i.e. to an elevator car 11 and a counterweight 12, to suspend these. Method steps for condition monitoring of an elevator rope are performed before installation of the elevator. The rope condition monitoring means 7 is used to measure electrical resistance between the first point and the second point of the ropes 3, 3' first time in the production site of the rope. In a preferred embodiment, the rope condition monitoring means 7 is used to measure electrical resistance between the first point and the second point of the ropes 3, 3' second time while the ropes are stored on the rope storage unit 1 before installation.

In installation of the elevator, a first end of the rope 3, 3' is connected to the car 11 and the second end to the counterweight 12. A plurality of ropes 3, 3' is installed this way simultaneously. The elevator comprises a hoistway S, an elevator car 11 and a counterweight 12 installed to be vertically movable in the hoistway S. The elevator further includes a drive machine M which is installed with the method to drive the elevator car 11 under control of an elevator control system (not shown). During said unwinding the rope 3, 3' is guided to pass over a drive wheel 10 of the drive machine M. The drive machine M is in this embodiment mounted inside a machine room MR, but the elevator could alternatively have a machine roomless configuration. The drive wheel 10 is arranged to engages said ropes 3, 3' passing over the drive wheel 10 and suspending the elevator car 11 and the counterweight 12. Thus, driving force can be transmitted from the motor to the car 11 and counterweight 12 via the drive wheel 10 and the ropes 3, 3' so as to move the car 11 and counterweight 12. Said unwinding comprises unwinding the rope 3, 3' by rotating the rope support body 6 supporting the rope reel 2. Before unwinding the rope storage unit is mounted rotatably (via a support shaft comprised in the support body). Also, before said unwinding the rope 3, 3' is guided to pass via a rope guide mounted stationary at proximity of the rope reel 2. The elevator car 11 and the counterweight 12 may be at any suitable position during said unwinding. However, when the connecting of the rope 3, 3' to the car is performed, preferably the car 11 is at an upper end of the hoistway S and the counterweight 12 resting on its buffer at the lower end of the hoistway S so as to fit their positions to suit the rope length. After installation, method steps for condition monitoring of the ropes 3, 3' is repeated to detect potentially damaged rope 3, 3' during installation.

In a preferred embodiment, the elevator rope condition monitoring arrangement has been arranged to comprise connector means, such as screws connected to load bearing parts 8, 8', 8", 8''' of said ropes 3, 3' at a first point R and at a second point R' of said ropes 3, 3', a rope condition monitoring device 7 comprising a current source 71, a voltage measurement device 72, a microcontroller 73, and a display 74 for monitoring condition of said ropes 3, 3'. If the data in the rope condition monitoring means needs to be logged, it can be done with a computer 70 connected to the rope condition monitoring means.

In a preferred embodiment voltage across the rope 3, 3' is measured by the microcontroller 73 from the measurement point R'. The analog to digital-converter ADC of the microcontroller 73 has preferably a resolution of twelve bits. The reference voltage of the ADC is the same as that of used in current source, again to eliminate the effect of operating voltage fluctuations.

Since the current source 71 provides stable measurement current, changes in the rope resistance cause change in the measured voltage.

In a preferred embodiment said rope condition monitoring device 7 has two operating modes, a learning mode and a monitoring mode. The learning mode is started with a four seconds long push of a button located on the printed circuit board PCB of said rope condition monitoring device 7. In this mode, at least the following operations are done.

a) Non-volatile memory of the microcontroller 7, containing the number of connected ropes 3, 3', the control value of each current source and the voltage measurement result for each rope 3, 3', is erased.

b) Starting from monitoring channel 1 current source is adjusted in such a way that current flowing through the measured rope 3, 3' increases and the voltage is measured at the same time. When the voltage across the rope is over a limit value, preferably 2.5 V or half of the operating/reference voltage, the current adjustment is stopped, and present current value and measured voltage value as well as the threshold values are stored in non-volatile memory. The number of ropes 3, 3', also stored in non-volatile memory, is increased by one, if there is a rope connected to that channel. These steps are repeated for each of the channels, preferably for each of said channels.

c) When the learning sequence is completed, said rope monitoring device 7 continues operation in the monitoring mode.

In a preferred embodiment, the voltage across each rope 3, 3' is measured in the monitoring mode. The measuring rate is preferably ca. 1200 1/s. Interference is avoided by calculating the floating average of the last results. The filtered results are compared to the threshold values in non-volatile memory, and if said filtered results meet said threshold values, an error code as follows and predetermined actions are carried out.

Level 1: Minor error, if deviation from said threshold values less than 5%.

Level 2: Low resistance, if deviation from said threshold values is equal to or less than 20%: Rope coating is worn or broken and the rope grounded.

Level 3: High resistance, if deviation from the threshold values is over 20%: Rope load-bearing part is broken or measurement wires disconnected.

In a preferred embodiment, each error level has its own indicator LED on the display 74 of the rope condition monitoring device 7. Rope number is shown on the LED display 74, and the status of that rope is indicated by the error LEDs at the same time. Preferably error codes are stored in the memory, but they can be erased by resetting said rope condition monitoring device 7.

In a preferred embodiment, the elevator installation or operation can be altered or the elevator rope can be taken out of service, depending on the severity of the fault, if error signals are detected.

In a preferred embodiment, after power is set on rope condition monitoring device 7 first sets the current for each measurement channel after reading the respective values from the non-volatile memory. Then it starts operating in the monitoring mode. Said rope condition monitoring device 7 is reset by pressing the button on the PCB and longer push starts the learning sequence.

In a preferred embodiment, if said rope condition monitoring device 7 needs to be replaced, the microcontroller 73 can be removed from its socket and installed in the new device. This way the initial values saved in the non-volatile memory can still be used and the monitoring can continue without losing the history data. If the data needs to be logged, it can be done with a computer 70 connected to the rope condition monitoring device 7. Said rope condition monitoring device 7 preferably transmits the status of each rope 3, 3', the initial resistance value and the current resistance value once per second to the elevator controller.

Figure 3:
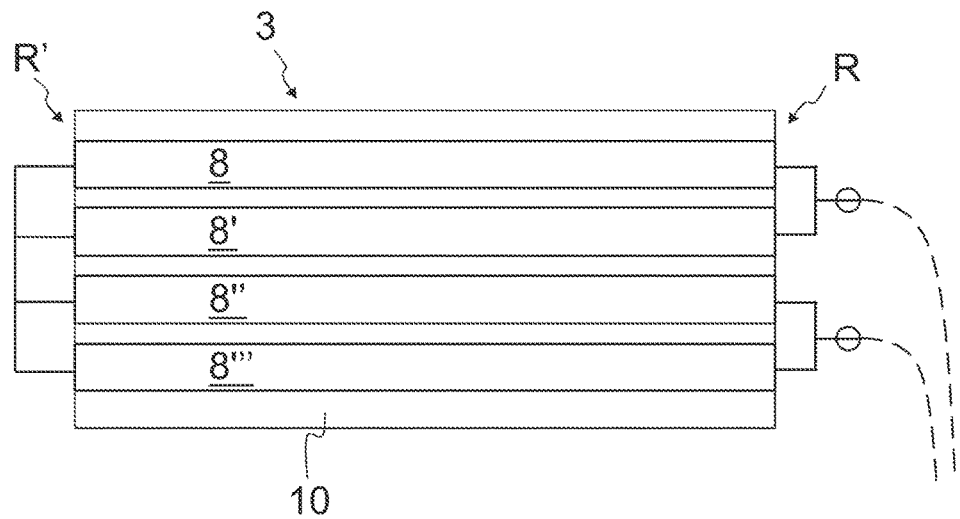
FIG. 3 illustrates an electrical model of the elevator rope condition monitoring arrangement according to an embodiment of the invention.
Figure 4:
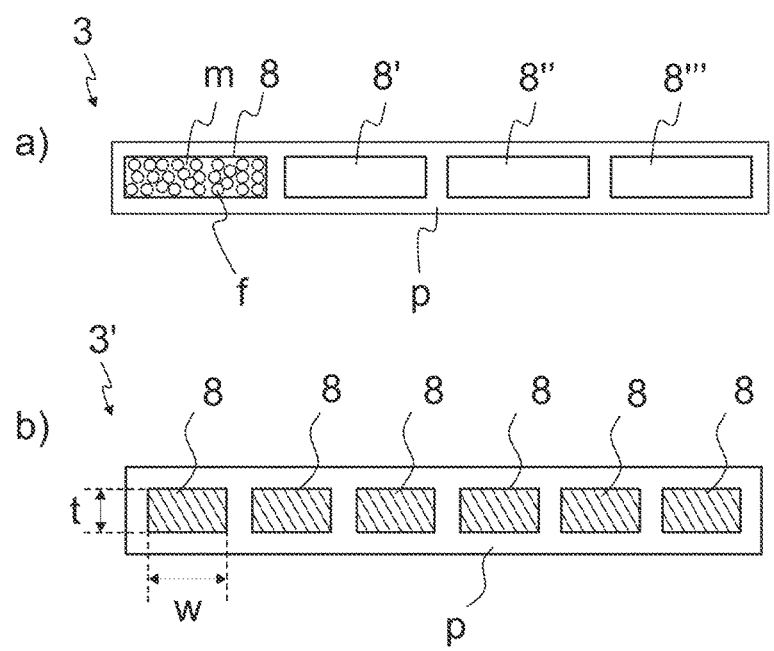
FIG. 4 illustrates a schematic view of a cross section of an embodiment of an elevator rope for which method steps of the invention can be performed.

FIG. 3 illustrates a preferred embodiment of an electrical model of the elevator rope condition monitoring arrangement, especially for the rope 3, 3' part of said rope condition monitoring means. In a preferred embodiment of the rope condition monitoring arrangement the elevator comprises a light-weight rope 3, 3' comprising one or more, preferably at least four unidirectional carbon fiber-reinforced-polymer load-bearing parts 8, 8', 8", 8''' as shown in FIG. 4 covered with polyurethane coating p. In case of four load-bearing parts 8, 8', 8", 8''' as shown in FIG. 3, the rope 3, 3' is electrically modeled as four resistors. Preferred solution is to measure one rope 3, 3' as a single resistance. In that way measuring arrangements are kept simple and the method is also more reliable, because the number of wires and connections is minimized. With this method simple and reliable solutions to short-circuit carbon fiber-reinforced-polymer load-bearing parts 8, 8', 8", 8''', and to connect the measuring wires to the rope 3, 3', preferably by self-tapping screws screwed between the load-bearing parts 8, 8', 8", 8''' in such a way, that the screw acts as an electrically conductive path between adjacent load-bearing parts 8, 8', 8", 8''', are used. At the counterweight end R' of said rope 3, 3', preferably three screws are used to short-circuit all of the strands. At the car end R of said rope 3, 3', preferably two outermost load-bearing parts are connected together, and measuring wires are inserted under these two screws with a split ring connector. With this arrangement, all carbon fiber-reinforced-polymer load-bearing parts 8, 8', 8", 8''' are monitored and the whole rope is seen as a single resistor.

FIG. 4a-b illustrates preferred embodiments of a rope 3, 3' cross section as described in connection with one of FIGS. 1 and 2 used as a suspension and/or transmission rope 3, 3' of an elevator, particularly a passenger elevator. In the use according to the invention, at least one rope 3, 3', but preferably a number of ropes 3, 3' is constructed such that the width of the rope is larger than its thickness in a transverse direction of the rope 3, 3' and fitted to support and move an elevator car, said rope 3, 3' comprising a load-bearing part 8, 8', 8", 8''' made of composite material, which composite material comprises reinforcing fibers, preferably unidirectional carbon fibers, in a polymer matrix. The suspension and/or transmission rope 3, 3' is most preferably secured by one end to the elevator car 11 and by the other end to a counterweight 12, but it is applicable for use in elevators without counterweight as well. Although the figures only show elevators with a 1:1 suspension and/or transmission ratio, the rope 3, 3' described is also applicable for use as a suspension and/or transmission rope 3, 3' in an elevator with a 1:2 suspension ratio. The rope 3, 3' is particularly well suited for use as a suspension and/or transmission rope 3, 3' in an elevator having a large suspension height, preferably an elevator having a suspension height of over 100 meters. The rope 3, 3' defined can also be used to implement a new elevator without a compensating rope, or to convert an old elevator into one without a compensating rope. The rope 3, 3' is well applicable for use in an elevator having a suspension height of over 30 meters and implemented without a compensating rope.

It is obvious to a person skilled in the art that the invention is not exclusively limited to the embodiments described above, in which the invention has been described by way of example, but that many variations and different embodiments of the invention are possible within the scope of the inventive concept defined in the claims presented below. Thus it is obvious that the ropes 3, 3' described may be provided with a cogged surface or some other type of patterned surface to produce a positive contact with the traction sheave 10. It is also obvious that the rectangular composite load-bearing parts 8, 8', 8", 8''' electrically modeled as resistors may comprise edges more starkly rounded than those illustrated or edges not rounded at all. Similarly, the polymer layer p of the ropes 3, 3' may comprise edges/corners more starkly rounded than those illustrated or edges/corners not rounded at all. It is likewise obvious that the load-bearing part/parts 8, 8', 8", 8''' in the embodiments in FIGS. 3 and 4 can be arranged to cover most of the cross-section of the rope 3, 3'. In this case, the sheath-like polymer layer p surrounding the load-bearing part/parts 8, 8', 8", 8''', is made thinner as compared to the thickness of the load-bearing part 8, 8', 8", 8''', in the thickness-wise direction of the rope 3, 3'.

It is likewise obvious that, in conjunction with the solutions represented by FIGS. 3 and 4, it is possible to use belts of other types than those presented. It is likewise obvious that both carbon fiber and glass fiber can be used in the same composite part if necessary. It is likewise obvious that the thickness of the polymer p layer may be different from that described. It is likewise obvious that the shear-resistant part could be used as an additional component with any other rope structure showed in this application. It is likewise obvious that the matrix polymer m in which the reinforcing fibers f are distributed may comprise—mixed in the basic matrix polymer, such as e.g. epoxy—auxiliary materials, such as e.g. reinforcements, fillers, colors, fire retardants, stabilizers or corresponding agents. It is likewise obvious that, although the polymer matrix preferably does not consist of elastomer, the invention can also be utilized using an elastomer matrix. It is also obvious that the fibers f need not necessarily be round in cross-section, but they may have some other cross-sectional shape. It is further obvious that auxiliary materials, such as e.g. reinforcements, fillers, colors, fire retardants, stabilizers or corresponding agents, may be mixed in the basic polymer of the layer p, e.g. in polyurethane. It is likewise obvious that the invention can also be applied in elevators designed for hoisting heights other than those considered above.

It is to be understood that the above description and the accompanying figures are only intended to illustrate the present invention. It will be apparent to a person skilled in the art that the inventive concept can be implemented in various ways. The invention and its embodiments are not limited to the examples described above but may vary within the scope of the claims.

The invention claimed is:

1. A method to monitor a condition of an elevator rope the elevator rope being an elevator suspension rope and/or an elevator transmission rope, the elevator rope including one or more load bearing parts, the method comprising:

reeling or packing the elevator rope in a rope storage unit, the rope storage unit including a support body and a rope reel, the support body including one or more support members, the one or more support members delimiting an inner space, the rope reel inside the inner space and supported by the support body such that the one or more support members radially surround the rope reel, the reeling or packing including winding the elevator rope in a spiral form around the rope reel in the inner space such that the one or more support members block the elevator rope from straightening;

performing a first measurement of electrical resistance between a first point of the elevator rope and a second point of the elevator rope at a rope condition monitoring device to determine a first electrical resistance value concurrently with the elevator rope remaining wound in the inner space of the rope storage unit, the rope condition monitoring device connected to the rope storage unit, the rope condition monitoring device further connected to the first point of the elevator rope and the second point of the elevator rope concurrently with the elevator rope remaining wound in the inner space of the rope storage unit;

determining a threshold value based on the first electrical resistance value;

delivering the rope storage unit in which the elevator rope remains wound into an installation site subsequently to determining the threshold value;

performing a second measurement of electrical resistance between the first point of the elevator rope and the second point of the elevator rope at the rope condition monitoring device to determine a second electrical resistance value subsequently to the delivering and concurrently with the elevator rope remaining wound in the inner space of the rope storage unit; and selectively performing an action based on determining that the second electrical resistance value at least meets the threshold value.

2. The method according to claim 1, wherein the first measurement of electrical resistance is performed in a rope production site.

3. The method according to claim 1, wherein at least the first electrical resistance value is marked on a deliver note, on the rope storage unit, on the elevator rope, or in a memory.

4. The method according to claim 3, wherein at least the first electrical resistance value is marked in a memory and/or in a database of a computer connected to the rope condition monitoring device.

5. The method according to claim 1, wherein performing the second measurement of electrical resistance includes measuring electrical resistance between the first point of the elevator rope and the second point of the elevator rope based on a determination that rope installation is ready, before mounting the elevator rope into rope terminals.

6. The method according to claim 1, wherein the first point of the elevator rope and the second point of the elevator rope are
points of a non-metallic load bearing part of the elevator rope, or
points of several electrically connected non-metallic load bearing parts of the elevator rope.

7. The method according to claim 1, wherein the first point of the elevator rope and the second point of the elevator rope are points of load bearing parts of the elevator rope, the load bearing parts including fiber-reinforced polymer matrix composite material.

8. The method according to claim 7, wherein the fiber-reinforced polymer matrix composite material includes a carbon fiber-reinforced polymer matrix composite.

9. The method according to claim 1, wherein the action that is selectively performed based on determining that the second electrical resistance value at least meets the threshold value includes generating an error signal.

10. The method according to claim 9, generating the error signal includes displaying a rope identification code and an error level indication associated with the elevator rope on an LED or LCD display of the rope condition monitoring device.

11. The method according to claim 9, wherein,
the error signal includes an indication that the elevator rope is damaged, and
the method further includes preventing the elevator rope from being installed into an elevator based on the indication.

12. The method according to claim 1, wherein the rope condition monitoring device is connected to the rope storage unit, the rope condition monitoring device further connected to the first point of the elevator rope and the second point of the elevator rope concurrently with the elevator rope remaining wound in the inner space of the rope storage unit, the rope condition monitoring device including an independently operating data logger-type condition monitoring device.

13. An apparatus configured to enable condition monitoring of an elevator rope, the elevator rope being an elevator suspension rope and/or an elevator transmission rope, the elevator rope including one or more load bearing parts, the apparatus comprising:
a rope storage unit including a support body and a rope reel, the support body including one or more support members, the one or more support members delimiting an inner space, the rope reel inside the inner space and supported by the support body such that the one or more support members radially surround the rope reel, the rope storage unit configured to receive the elevator rope into the inner space such that the elevator rope is wound in a spiral form by the rope reel in the inner space and the one or more support members block the elevator rope from straightening,
a rope condition monitoring device connected to the rope storage unit, the rope condition monitoring device further connected to a first point of the elevator rope and a second point of the elevator rope concurrently with the elevator rope remaining wound in the inner space of the rope storage unit, the rope condition monitoring device configured to
perform a first measurement of electrical resistance between the first point of the elevator rope and the second point of the elevator rope to determine a first electrical resistance value concurrently with the elevator rope remaining wound in the inner space of the rope storage unit,
determine a threshold value based on the first electrical resistance value;
perform a second measurement of electrical resistance between the first point and the second point of the elevator rope to determine a second electrical resistance value subsequently to determining the threshold value and concurrently with the elevator rope remaining wound in the inner space of the rope storage unit; and generate a signal based on a determination that the second electrical resistance value at least meets the threshold value.

14. The apparatus according to claim 13, wherein each measurement of the first measurement of electrical resistance and the second measurement of electrical resistance includes concurrently with the rope storage unit being located in a rope production site.

15. The apparatus according to claim 13, wherein at least the first electrical resistance value is marked on a deliver note, on the rope storage unit, on the elevator rope, or in a memory.

16. The apparatus according to claim 15, wherein at least the first electrical resistance value is marked in a memory and/or in a database of a computer connected to the rope condition monitoring device.

17. The apparatus according to claim 13, wherein performing the second measurement of electrical resistance includes measuring electrical resistance between the first point of the elevator rope and the second point of the elevator rope based on a determination that rope installation is ready, before mounting the elevator rope into rope terminals.

18. The apparatus according to claim 13, wherein the first point of the elevator rope and the second point of the elevator rope are
points of a non-metallic load bearing part of the elevator rope, or
points of several electrically connected non-metallic load bearing parts of the elevator rope.

19. The apparatus according to claim 13, wherein the first point of the elevator rope and the second point of the elevator rope are points of load bearing parts of the elevator rope, the load bearing parts including fiber-reinforced polymer matrix composite material.

20. The apparatus according to claim 19, wherein the fiber-reinforced polymer matrix composite material includes a carbon fiber-reinforced polymer matrix composite.

21. The apparatus according to claim 13, wherein the signal is an error signal.

22. The apparatus according to claim 13, wherein the rope condition monitoring device includes an independently operating data logger-type condition monitoring device.

23. The apparatus according to claim 13, wherein the rope condition monitoring device is configured to generate a rope identification code and error level indication associated with the elevator rope on a LED or LCD display of the rope condition monitoring device based on determining that the second electrical resistance value at least meets the threshold value.

24. The apparatus according to claim 23, wherein the error level indication includes an indication that the elevator rope is damaged.

* * * * *